United States Patent [19]

Miike et al.

[11] Patent Number: 4,877,727

[45] Date of Patent: Oct. 31, 1989

[54] SUBSTRATE FOR DETERMINING LEUCINE AMINOPEPTIDASE OR GAMMA-GLUTAMYLTRANSPEPTASE ACTIVITY

[75] Inventors: Akira Miike, Shizuoka; Yukio Katsumata, Susono; Toshio Tatano, Numazu, all of Japan

[73] Assignee: Kyowa Medex Co., Ltd., Tokyo, Japan

[21] Appl. No.: 248,347

[22] Filed: Sep. 20, 1988

Related U.S. Application Data

[63] Continuation of Ser. No. 698,623, Feb. 6, 1985, abandoned.

[30] Foreign Application Priority Data

Feb. 7, 1984 [JP] Japan ................................ 59-20194

[51] Int. Cl.$^4$ ........................... C12Q 1/36; C12Q 1/26
[52] U.S. Cl. ........................................ 435/24; 435/25
[58] Field of Search ....................... 435/15, 18, 23, 24, 435/25, 810; 436/903; 530/402, 415

[56] References Cited

U.S. PATENT DOCUMENTS 4,588,836  5/1986  Matsumoto et al. ................ 562/448
4,675,290  6/1987  Matsumoto et al. ................. 435/24

Primary Examiner—David M. Naff
Attorney, Agent, or Firm—Michael N. Meller

[57] ABSTRACT

Leucine aminopeptidase (LAP) activity or $\gamma$-glutamyltranspeptidase ($\gamma$-GTP) activity in a sample is determined by converting a substrate represented by the formula (I):

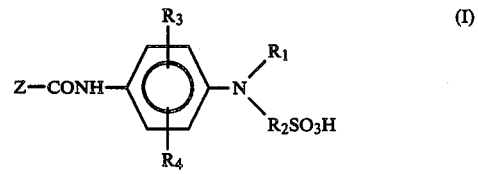

wherein Z represents $(CH_3)_2CHCH_2CH(NH_2)-$ or $(NH_2)(COOH)CHCH_2CH_2-$, $R_1$ represents hydrogen, alkyl or substituted alkyl, $R_2$ represents alkylene or hydroxyalkylene, $R_3$ and $R_4$ are the same or different and represents hydrogen, halogen, nitro, hydroxyl, sulfo, carboxyl, alkyl, and alkoxy, and salts thereof into a compound represented by the formula (II):

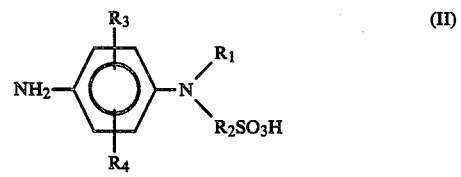

wherein $R_1$, $R_2$, $R_3$ and $R_4$ have the same meanings as defined above. The compound (II) is reacted with a chromogen to form a pigment or converted into a diazonium salt which is reacted with a coupling agent to form an azo dye. Absorption of a resultant colored reaction solution is measured.

14 Claims, No Drawings

SUBSTRATE FOR DETERMINING LEUCINE AMINOPEPTIDASE OR GAMMA-GLUTAMYLTRANSPEPTASE ACTIVITY

This application is a continuation of application Ser. No. 698,623, filed Feb. 6, 1985, now abandoned.

BACKGROUND OF THE INVENTION

The present invention relates to a method for the determination of enzyme activity and a composition suitable therefor. In the present specification, the enzymes to be determined are leucine aminopeptidase (hereinafter referred to as LAP) and γ-glutamyltranspeptidase (hereinafter referred to as γ-GTP).

Heretofore, as a method for measuring the enzyme activities, it has been known that a substrate for enzymes obtained by binding leucine or glutamic acid with a chromogen is decomposed by the action of the enzyme in a sample to form a colored compound which is determined.

As the chromogen, p-nitroanilide, β-naphthylamide, 4-hydroxy-3-carboxyanilide, p-hydroxyanilide, 4-N,N-dialkylamino-3-carboxyanilide, 4-N,N-dialkylaminoanilide and the like are used.

The solubility of these compounds is, at most, 6.5 mg/ml and the rate of enzymatic reaction is controlled by the rate of solubility. Further, in the determination of the pigment formed by using these substrates, the results are likely to be influenced by the other components in the sample. Because the determination is made by measuring the absorbancy in the ultraviolet region, a enzymatic reaction must be carried out under the strong alkaline condition which is a dangerous condition. The sensitivity is low because the molecular extinction coefficient of the formed pigments is low a long period of time is required to complete the enzymatic reaction, and thus the accuracy of the results by the method is low.

As a result of studies of substrates having few faults, it has been found that p-aminoanilide compounds wherein an alkyl or hydroxyalkyl group containing a sulfo group is bonded to the amino group in the para-position, have excellent solubility and stability of the pigment formed by the enzymatic reaction. It is possible to measure in the visible region because the chromogen has a high molecular extinction coefficient.

SUMMARY OF THE INVENTION

According to the present invention, LAP or γ-GTP can be determined by converting the substrate for the enzyme to be determined represented by the general formula (I)

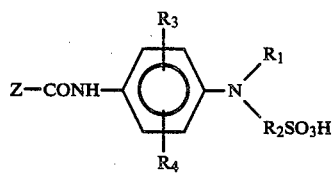

wherein Z represents $(CH_3)_2CHCH_2CH(NH_2)-$ (hereinafter referred to as $Z_1$) or $(NH_2)(COOH)CHCH_2CH_2-$ (hereinafter referred to as $Z_2$), $R_1$ represents hydrogen, alkyl or substituted alkyl, $R_2$ represents alkylene or hydroxyalkylene, $R_3$ and $R_4$ are the same or different and represents hydrogen, halogen, nitro, hydroxyl, sulfo, carboxyl, alkyl, and alkoxy, and salts thereof into the compound represented by the general formula (II) [hereinafter referred to as compound (II)]

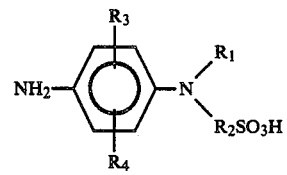

wherein $R_1$, $R_2$, $R_3$ and $R_4$ have the same meaning as described above by the action of LAP or γ-GTP, (a) reacting the compound (II) with a chromogen to form a pigment or (b) converting the compound (II) into a diazonium salt and reacting the diazonium salt with a coupling agent to form an azo dye, and measuring the absorbancy of the colored reaction solution.

DETAILED DESCRIPTION OF THE INVENTION

In the definition of $R_1$–$R_4$, alkyl includes alkyl having 1–5 carbon atoms such as methyl, ethyl, propyl, butyl and amyl, halogen includes chloro, iodo and bromo groups, the alkyl moiety in alkoxy has the same meaning as those of alkyl defined above, alkylene includes alkylene having 1–5 carbon atoms such as methylene, ethylene, tetramethylene and pentamethylene, the alkylene moiety in hydroxyalkylene has the same meaning as those of alkylene defined above, and the substituent of substituted alkyl includes sulfo, hydroxyaryl, nitro, carboxyl, halogen such as chloro and bromo.

Compound (I) can be synthesized by the following method.

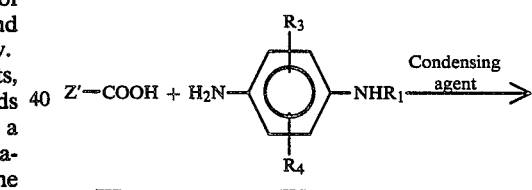

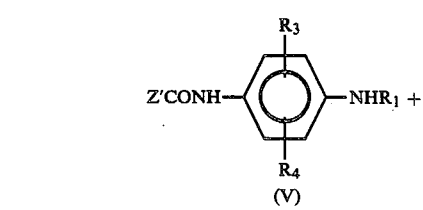

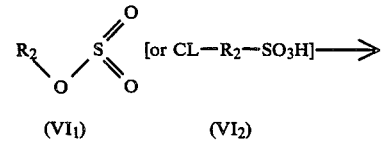

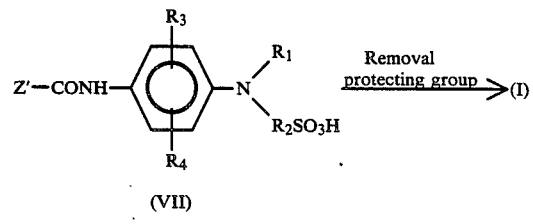

Z' represents the group where the amino group in Z is protected with an amino protecting group and/or the carboxyl group in Z is protected with a carboxyl protecting group. Examples of the protecting group include amino protecting groups such as benzyloxycarbonyl group, tert-butoxycarbonyl (BOC) groups and carboxyl protecting group such as benzyl group and acyl group (acetyl).

Examples of compound (III) include N-BOC-L-leucine, N-BOC-L-glutamic acid-α-benzylester. As compound (IV), phenylenediamine or phenylenediamines having substituents corresponding to $R_3$ or $R_4$ of the substituents of desired compound may be used. As condensing agent, for example, DCC may be used.

The reaction is carried out at room temperature to 60° C. for 1 to 10 hours in an organic solvent. The reaction mixture per se or compound V isolated therefrom is dissolved in an organic solvent such as chloroform and compound VI is added thereto. The reaction is carried out at room temperature to 60° C. for 15-30 hours.

As a compound VI, compound corresponding to substituent $R_2$ of the desired compound is used and examples are shown in reference example 2 described later. The desired compound is obtained by isolating compound VII after completion of the reaction and removing the amino and/or carboxyl protecting group by methods known per se.

Examples of the chromogen include amines such as N,N-diethyl-m-toluidine, N-ethyl-N-hydroxyethyl-m-toluidine, N-ethyl-N-3-methylphenyl-N'-acetylethylenediamine (EMAE), N-ethyl-N-(3-methylphenyl)-N'-succinylethylenediamine (EMSE), N,N-di-3-sulfopropyl-m-toluidine, N-ethyl-N-2-hydroxy-3-sulfopropyl-m-toluidine (TOOS), N,N-dimethyl-m-toluidine, N-ethyl-N-2-cyanoethyl-m-toluidine, N-(2-hydroxy-3-sulphopropyl)-m-toluidine, aniline derivatives such as N-ethyl-N-(3-sulfopropyl)-3,5-dimethoxyaniline, N-ethyl-N-(2-hydroxy)-3-sulfopropyl-3,5-dimethoxyaniline, N-ethyl-N-(3-sulfopropyl)-3-methoxyaniline, N-ethyl-N-2-cyanoethyl-aniline, N,N-dimethylaniline and N,N-diethylaniline, phenols such as α-naphthol, β-naphthol, o- or p-bromophenol, o- or m-anisole, 2,6-xylenol, 3,5-xylenol, 2,5-xylenol, 2,3-xylenol and o- or m-cresol.

These chromogens are used in a concentration of 0.01-5 mg/ml with surfactant such as Triton X-100, Brij-35 and Brij-80 in a concentration of 0.01-2% for chromogens having low solubility.

As a chromogen, cinnamaldehydes such as p-N,N-dimethylamino cinnamaldehyde, p-N,N-diethylamino cinnamaldehyde may also be used in a concentration of 0.01-100 mg/ml. In this case, an azo dye is formed as the pigment.

As diazonization agent used in the conversion of compound (II) into a diazonium salt, sodium, potassium or ammonium nitrites may be used in a concentration of 0.1-100 mg/ml. As coupling agent, phenols described above such as phenol and 3,5-xylenol may be used in a concentration of 0.01-100 mg/ml.

When the formed pigment is not an azo dye, the reaction of compound (II) with a chromogen is usually carried out in the presence of an oxidizing agent including oxidase.

Examples of oxidizing agents include inorganic compounds such as hydrogen peroxide, sodium or potassium metaperiodate, sodium or potassium permanganate, sodium or potassium dichromate, sodium or potassium metavanadate, pentacyanoiron complex, peroxides of acids such as peracetic acid, hydrogen peroxide-peroxidase (HRP), and oxidases such as ceruloplasmin and laccase (E C. 1. 10. 3. 2).

They may be used in a concentration of 0.01-10 mg/ml for inorganic compounds, 0.1-100 U/ml for oxidases.

Tables 1 and 2 show the solubility, maximum wavelength, sensitivity and stability of the formed pigment.

TABLE

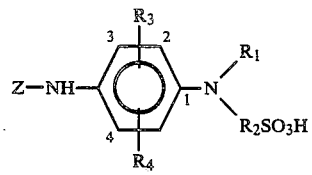

| Compound No. | Z | $R_3$ | $R_4$ | $R_1$ | $R_2$ |
|---|---|---|---|---|---|
| 1 | $Z_2$ | H | H | $(CH_2)_3SO_3H$ | $—(CH_2)_3—$ |
| 2 | $Z_1$ | " | " | " | " |
| 3 | $Z_2$ | " | " | $CH_3$ | " |
| 4 | $Z_1$ | " | " | " | " |
| 5 | $Z_2$ | " | " | $C_2H_5$ | $—CH_2CHCH_2—OH$ |
| 6 | $Z_1$ | " | " | " | " |
| 7 | $Z_2$ | $SO_3H(2)$ | " | $(CH_2)_3SO_3H$ | $—(CH_2)_3—$ |
| 8 | $Z_1$ | " | " | " | " |
| 9 | $Z_2$ | $Cl(2)$ | " | " | " |
| 10 | $Z_1$ | " | " | " | " |
| 11 | $Z_1$ | $CN(2)$ | " | $(CH_2)_2SO_3H$ | $—(CH_2)_2—$ |
| 12 | $Z_1$ | $CH_3(2)$ | " | " | " |
| 13 | $Z_1$ | $COOCH_3(2)$ | " | $(CH_2)_4SO_3H$ | $—(CH_2)_4—$ |
| 14 | $Z_1$ | $OCH_3(4)$ | $CH_3(2)$ | " | " |

TABLE -continued

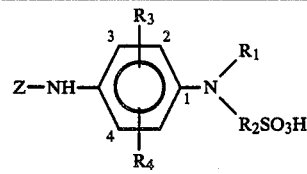

| Compound No. | Z | R₃ | R₄ | R₁ | R₂ |
|---|---|---|---|---|---|
| Control | | | | | |

$$Z_1-NH-\langle\bigcirc\rangle-OH$$
$$\qquad\qquad COOH$$

Numbers in parenthesis of $R_3$ or $R_4$ show the position of the $R_3$ or $R_4$ group on the benzenenucleus.

TABLE 2

| | $\lambda_{max}$ (nm) | SE | ST(%) | S (mg/ml) |
|---|---|---|---|---|
| 1 | 745 | >500 | 98< | >200 |
| 2 | 745 | >500 | 98< | 130 |
| 3 | 750 | >500 | 96< | 80 |
| 4 | 750 | >500 | 96< | 65 |
| 5 | 740 | >500 | 98< | 170 |
| 6 | 740 | >500 | 98< | 90 |
| 7 | 680 | 237 | 93 | >20 |
| 8 | 680 | 237 | 93 | >200 |
| 9 | 685 | 315 | 98< | >200 |
| 10 | 685 | 315 | 98< | 125 |
| 11 | 640 | 177 | 95 | >200 |
| 12 | 715 | >500 | >98 | >200 |
| 13 | 705 | 312 | >98 | >200 |
| 14 | 720 | 406 | >98 | >200 |
| Control | 615 | 100 | 90 | <20 |

$\lambda_{max}$: Maximum wavelength
SE: Sensitivity of pigment
ST: Stability of pigment
S: Solubility

Sensitivity

50 μl of 1 mM each free compound was added to 3 ml of 0.1M phosphate buffer containing 0.5 mg/ml EMSE and 1 U/ml laccase and the mixture was incubated at 37° C. for 5 minutes. The absorption of the reaction solution at λmax was measured. As a control, 5-aminosalicylic acid was used and the reaction of the compound with 2,6-xylenol was carried out in the presence of metaperiodate under strong alkaline conditions.

The results are shown, defining the sensitivity of 5-aminosalicylic acid as 100.

The enzymatic reaction is usually carried out in a buffer solution having a pH of 6 to 10 preferably around 8. As the buffer, good buffer, phosphate buffer, acetate buffer, etc. may be used.

The present method is very simple and excellent. For example, the solubility of the present substrate is very high and therefor it is not necessary to add a surfactant or organic solvent to increase the solubility. The measurement of absorption is carried out at a wavelength of 560 nm or more and therefore the results are not influenced by the component in the serum. Since the sensitivity and stability of the present substrate are excellent, it is expected that more accurate results will be obtained.

Another aspect of the present invention is to provide a test composition for the determination of LAP activity or γ-GTP activity which comprises the substrate represented by the general formula (I) and a chromogen. The composition may also contain an oxidizing agent, an oxidase, a diazonizing agent, a coupling agent or a buffer.

Certain specific embodiments of the invention are illustrated by the following representative examples.

EXAMPLE 1

| Reagent solution (pH 7.3) | | |
|---|---|---|
| Compound No. 2 | 0.03 | g/ml |
| EMSE | 0.5 | mg/ml |
| Magnesium nitrate | 1 | mg/ml |
| Good buffer | 8 | mg/ml |
| Laccase | 1 | U/ml |

3 ml of the reagent solution was incubated at 37° C. for ten minutes. To the solution was added 0.05 ml of a serum sample and the mixture was immediately stirred and the change in absorption of the solution at 745 nm was measured for one minute.

LAP activity in the sample can be calculated using the following equation:

$$LAP\,(U/l) = \frac{\Delta E \times 3.05 \times 1000}{7.2 \times 0.05} = \Delta E \times 847$$

ΔE means the amount of absorption change per minute.

The same procedures as described above were repeated except that the following materials were used.

| (a) | Substrate | L-leucil-3-carboxy-4-hydroxyanilide |
| | Oxidizing agent | sodium metaperiodate |
| | Coupling agent | p-xylenol |
| | Wavelength for measurement | 635 nm |
| (b) | Substrate | L-leucil-p-nitroanilide |
| | Coupling agent | p-dimethylaminocinnamaldehyde |
| | Wavelength for measurement | 565 nm |
| (c) | Substrate | L-leucil-p-N,N—diethylaminoanilide |
| | Oxidizing agent | m-periodate |
| | Coupling agent | 1-naphtol-2-sulfonic acid |
| | Wavelength for measurement | 675 nm |

The amounts of absorption change per minute were measured for ten samples and the results are shown in Table 3.

TABLE 3

| | (a) | (b) | (c) | The method according to the present invention |
|---|---|---|---|---|
| Serum(1) | 0.0188 | 0.0071 | 0.0158 | 0.0454 |
| (2) | 0.0127 | 0.0054 | 0.0095 | 0.0395 |
| (3) | 0.0198 | 0.0090 | 0.0150 | 0.0543 |
| (4) | 0.0203 | 0.0089 | 0.0145 | 0.0541 |
| (5) | 0.0148 | 0.0071 | 0.0116 | 0.0382 |
| (6) | 0.0158 | 0.0071 | 0.0126 | 0.0437 |
| (7) | 0.0153 | 0.0074 | 0.0113 | 0.0400 |
| (8) | 0.0191 | 0.0086 | 0.0150 | 0.0532 |
| (9) | 0.0190 | 0.0082 | 0.0138 | 0.0537 |
| (10) | 0.01840 | 0.0079 | 0.0133 | 0.0476 |

EXAMPLE 2

The reagent solution wherein laccase was excluded from the reagent solution of Example 1 was used.

3 ml of the reagent solution was incubated at 37° C. for 10 minutes and to the mixture was added 0.05 ml of a serum sample. The mixture was immediately stirred and incubated at 37° C. for 10 minutes. After ten minutes passed, (a) 0.03 ml of 10 mg/ml α-naphthol methanol solution and 0.1 ml of 1N-NaOH solution containing 50 mg/ml sodium salt of meta-periodate were added to the solution. The mixture was incubated at 37° C. for 10 minutes and the absorption of the reaction solution at 600 nm was measured.

(b) 1 ml of 10 mg/ml p-N,N-dimethylamino cinnamaldehyde ethanol solution and 1 ml of 0.4N-HCl solution were added to the solution and the mixture was incubated at 37° C. for 10 minutes. The absorption of the reaction solution at 570 nm was measured.

(c) 0.5 ml of 1N-HCl and 0.5 ml of 1 mg/ml sodium nitrite were added to the solution and the mixture was incubated at 37° C. for 10 minutes. Then 0.1 ml of 1 mg/ml 3,5-xylenol ethanol solution was added thereto and the absorption of the reaction solution at 650 nm was measured.

The results are shown in Table 4

Table 4

| | (a) | (b) | (c) | Example 1 |
|---|---|---|---|---|
| Serum 1 | 0.331 | 0.386 | 0.277 | 0.0454 |
| 2 | 0.291 | 0.336 | 0.241 | 0.0395 |
| 3 | 0.389 | 0.466 | 0.330 | 0.0543 |
| 4 | 0.395 | 0.460 | 0.325 | 0.0541 |
| 5 | 0.277 | 0.320 | 0.230 | 0.0382 |
| 6 | 0.322 | 0.372 | 0.270 | 0.0437 |
| 7 | 0.291 | 0.333 | 0.244 | 0.0400 |
| 8 | 0.386 | 0.453 | 0.325 | 0.0532 |
| 9 | 0.392 | 0.460 | 0.331 | 0.0537 |
| 10 | 0.346 | 0.405 | 0.292 | 0.0476 |
| Ratio of sensitivity | 73 | 85 | 61 | 100 |

EXAMPLE 3

In this example, 500 mg of compound Nos. 1, 3, 5, 7 and 9 each and 500 mg of glycylglycine were dissolved in 100 ml (pH=7.7) and 0.1M phosphate buffer. The resultant solutions were designated A-1, A-3, A-5, A-7 and A-9, respectively. 50 mg of 3-{N-(m-tolyl)-N-ethyl-}amino-2-hydroxypropane sulfonic acid was dissolved in 100 ml of phosphate buffer solution to obtain solution B. 50 mg/ml sodium meta-periodate containing 1N-HCl solution was prepared as solution C.

6 ml of solution A-1, A-3, A-5, A-7 or A-9 was equally poured to 3 test tubes. The samples were incubated at 37° C. and to the solution was added 20 μg of (a) serum sample (b) standard serum or (c) water. The mixtures were stirred and heated for 5 minutes. After 5 minutes had passed, 1 ml of solution B and 1 ml of solution C were added to each of the mixtures and the mixtures were incubated for 10 minutes after stirring. The absorption of the reaction solutions were measured at the wavelength indicated in Table 2. As the standard serum, a serum having 235 mU/ml of γ-GTP was used.

The γ-GTP activity of the serum sample can be calculated by the following equation.

$$\frac{\text{Absorption of } (a) - \text{Absorption of } (c)}{\text{Absorption of } (b) - \text{Absorption of } (c)} \times 235 \text{ mU/ml}$$

The results are 231, 228, 236, 240, and 242 mU/ml respectively.

REFERENCE EXAMPLE 1

Production of the hydrobromide of L-leucyl-p-N,N-disulfopropyl aminoanilide.

2.49 g of N-BOC-L-leucine (hereinafter referred to as BLL) was dissolved in 100 ml of dioxane. To the solution were added 4.12 g of DCC and 2.16 g of p-phenylenediamine (hereinafter referred to as PDD), and the mixture was incubated at room temperature for 4 hours. The mixture was filtered and the filtrate was concentrated to dryness under reduced pressure. The product was redissolved in methanol/water=80/20 (vol/vol) and the solution was subjected to chromatography using Diaion HP-20 (Produced by Mitsubishi Chemical Industries Ltd.) and methanol/water=80/20 was used as eluting agent.

Methanol was removed from the eluate under reduced pressure to obtain N-BOC-L-leucine-p-aminoanilide in the yield of 1.25 g. 1 g of the product was dissolved in 50 ml of chloroform. To the mixture were added 2 ml of triethylamine and 5 g of 1,3-propanesultone and the mixture was incubated at 50° for one day. 50 ml of ethyl ether was added to the mixture which was separated into two layers. To the lower layer were added 5 ml of acetic acid and 20 ml of 25% hydrogen bromide-acetic acid and the mixture was allowed to stand at room temperature. To the mixture was added 50 ml of ethyl ether to remove the BOC group and to form L-leucine-p-N,N-disulfopropyl aminoanilide.HBr as a precipitate. After filtration with a glass filter, the precipitate was dissolved in 50 ml of methanol and the solution was neutralized with 6N-NaOH. After removal of formed NaCl by filtration, ethyl ether was added to form a precipitate. The precipitate was separated by filtration to obtain 0.63 g of desired compound having a melting point of 221°–223° C.

| Elemental analysis | C | H | N |
|---|---|---|---|
| Found (%) | 46.29 | 6.58 | 9.07 |
| Calculated(%) | 46.45 | 6.67 | 9.03 |

REFERENCE EXAMPLE 2

The similar procedures as described in Reference example 1 were repeated except that N-BOC-L-glutamic acid-α-benzylester (BLGB) instead of BLL, or chloro-PPD (CLPPD), sulfo-PPD (SPPD), N-methyl-PPD (NMPPD), N-ethyl-PPD (NEPPD), N-cyano-PPD (CYPPD), methyl-PPD (MPPD), methyloxycarbonyl-PPD (MCPPC) or 2-methyl-5-methoxy-PPD (MOMPPD) instead of PPD and propanesultone (PS), 2-chloroethanesulfonic acid (CESA), 1,4-butanesultone (BS) or 3-chloro-2-hydroxy-propanesulfonic acid (CHPSA) as sulfonizing agent were used to obtain compounds indicated in Table 5.

TABLE 5

| Compound No. | Compound III | Compound IV | Sulfonizing agent | m.p. | $R_f$ of TLC |
|---|---|---|---|---|---|
| 1 | BLGB | PPD | PS | 201–205° C. | 0.19 |
| 2 | BLL | PPD | PS | 221–223° C. | 0.38 |
| 3 | BLGB | NMPPD | PS | 173–178° C. | 0.62 |
| 4 | BLL | NMPPD | PS | 169–172° C. | 0.80 |
| 5 | BLGB | NEPPD | CHPSA | 194–197° C. | 0.44 |
| 6 | BLL | NEPPD | CHPSA | 180–185° C. | 0.51 |
| 7 | BLGB | SPPD | PS | 228–230° C. | 0.08 |
| 8 | BLL | SPPD | PS | 217–222° C. | 0.12 |
| 9 | BLGB | CLPPD | PS | 225–228° C. | 0.45 |
| 10 | BLL | CLPPD | PS | 201–207° C. | 0.52 |
| 11 | BLL | CYPPD | CESA | 210–215° C. | 0.47 |
| 12 | BLL | MOMPPD | CESA | 153–157° C. | 0.70 |
| 13 | BLL | MCPPD | BS | 169–175° C. | 0.77 |
| 14 | BLL | MOMPPD | BS | 150–153° C. | 0.63 |

What is claimed is:

1. A test composition for the determination of leucine aminiopeptidase (LAP) or γ-glutamyltranspeptidase (γ-GTP) activity in a sample which comprises a substrate for the LAP or γ-GTP represented by the formula (I):

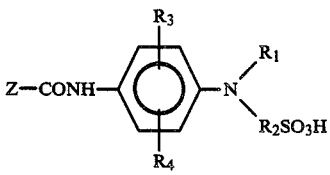

wherein Z represents $(CH_3)_2CHCH_2CH(NH_2)$— or $(NH_2)(COOH)\,CHCH_2CH_2$—, $R_1$ represents hydrogen, alkyl or substituted alkyl, $R_2$ represents alkylene or hydroxyalkylene, $R_3$ and $R_4$ are the same or different and represents hydrogen, halogen, nitro, hydroxyl, sulfo, carboxyl, alkyl, and alkoxy, and salts thereof, and a chromogen for reacting with a compound formed from the substrate (I) by action of the LAP or γ-GTP to form a pigment proportional to LAP or GTP activity in a sample.

2. A test composition according to claim 1, wherein said composition further contains an oxidizing agent.

3. A test composition according to claim 2, wherein said oxidizing agent is an oxidase.

4. A test composition according to claim 1, wherein said composition further contains a diazonizing agent.

5. A method for the determination of leucine aminopeptidase (LAP) activity or γ-glutamyltranspeptidase (γ-GTP) activity in a sample which comprises converting by action of the LAP or γ-GTP substrate represented by the formula (I):

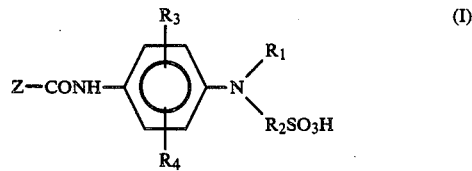

wherein Z represents $(CH_3)_2CHCH_2CH(NH_2)$— or $(NH_2)(COOH)\,CHCH_2CH_2$—, $R_1$ represents hydrogen, alkyl or substituted alkyl, $R_2$ represents alkylene or hydroxyalkylene, $R_3$ and $R_4$ are the same or different and represents hydrogen, halogen, nitro, hydroxyl, sulfo, carboxyl, alkyl, and alkoxy, and salts thereof into a compound represented by the formula (II):

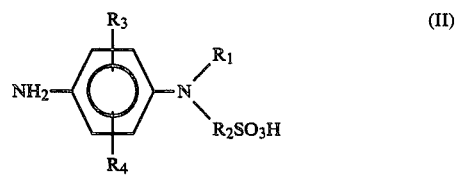

wherein $R_1$, $R_2$, $R_3$ and $R_4$ have the same meanings as defined above, reacting the compound (II) with a chromogen to form a pigment or converting the compound (II) into a diazonium salt and reacting the diazonium salt with a coupling agent to form an azo dye, and measuring the absorption of a colored reaction solution.

6. A method according to claim 5, wherein said reaction of compound (II) with the chromogen is carried out in the presence of an oxidizing agent.

7. A method according to claim 6, wherein said oxidizing agent is an oxidase.

8. A method according to claim 5, wherein Z is $(CH_3)_2CHCH_2CH(NH_2)$—.

9. A method according to claim 5, wherein Z is $(NH_2)(COOH)CH.CH_2.CH_2$—.

10. A method according to claim 5, wherein $R_1$ is sulfoalkyl.

11. A method according to claim 5, wherein said substrate is L-leucyl-p-N,N-disulfopropylamino anilide.

12. A method according to claim 5, wherein said chromogen is selected from the group consisting of N,N-diethyl-m-toluidine, N-ethyl-N-hydroxyethyl-m-toluidine, N-ethyl-N-3-methylphenyl-N'-acetylethylenediamine, N-ethyl-N-(3-methylphenyl)-N'-succinylethylenediamine, N,N-di-3-sulfopropyl-m-toluidine, N-ethyl-N-2-hydroxy-3-sulfopropyl-m-toluidine, N,N-dimethyl-m-toluidine, N-ethyl-N-2-cyanoethyl-m-toluidine, N-(2-hydroxy-3-sulphopropyl)-m-toluidine, N-ethyl-N-(3-sulfopropyl)-3,5-dimethoxyaniline, N-ethyl-N-(2-hydroxy)-3-sulfopropyl-3,5-dimethoxyaniline, N-ethyl-N-(3-sulfopropyl)-3-methoxyaniline, N-ethyl-N-2-cyanoethyl-aniline, N,N-dimethylaniline N,N-diethylaniline, α-naphthol, β-naphthol, o-bromophenol, p-bromophenol, o-anisole, m-anisole, 2,6-xylenol, 3,5-xylenol, 2,5-xylenol, 2,3-xylenol o-cresol and m-cresol.

13. A method according to claim 5, wherein said chromogen is N-ethyl-N-(3-methylphenyl)-N'-succinylethylenediamine.

14. A method according to claim 5, wherein said chromogen is cinnamaldehyde.

* * * * *